(12) United States Patent
Viebach et al.

(10) Patent No.: US 9,955,856 B2
(45) Date of Patent: May 1, 2018

(54) DEVICE AND A METHOD FOR MANUFACTURING AN ELONGATED HOLLOW PROFILE ELEMENT, AN ELONGATED HOLLOW PROFILE ELEMENT, AND A BENDING SECTION FOR AN ENDOSCOPE

(71) Applicant: DIGITAL ENDOSCOPY GMBH, Friedberg (DE)

(72) Inventors: Thomas Viebach, Waidhofen (DE); Fritz Pauker, Diedorf (DE)

(73) Assignee: Digital Endoscopy GmbH, Friedberg (DE)

( * ) Notice: Subject to any disclaimer, the term of this patent is extended or adjusted under 35 U.S.C. 154(b) by 0 days. days.

(21) Appl. No.: 15/106,268

(22) PCT Filed: Dec. 16, 2014

(86) PCT No.: PCT/EP2014/077938
§ 371 (c)(1),
(2) Date: Jun. 17, 2016

(87) PCT Pub. No.: WO2015/091464
PCT Pub. Date: Jun. 25, 2015

(65) Prior Publication Data
US 2016/0316997 A1    Nov. 3, 2016

(30) Foreign Application Priority Data
Dec. 19, 2013    (DE) .................. 10 2013 226 591

(51) Int. Cl.
*A61B 1/005* (2006.01)
*B29C 45/14* (2006.01)
(Continued)

(52) U.S. Cl.
CPC .......... *A61B 1/0055* (2013.01); *A61B 1/0011* (2013.01); *A61B 1/0057* (2013.01);
(Continued)

(58) Field of Classification Search
CPC . A61B 1/0055; A61B 1/0057; A61B 1/00071; A61B 1/0011; B29C 45/14754; B60T 11/046; F16C 1/26; F16C 1/10
See application file for complete search history.

(56) References Cited

U.S. PATENT DOCUMENTS

| 3,549,806 A | 12/1970 | Wood |
| 3,605,725 A | 9/1971 | Bentov |

(Continued)

FOREIGN PATENT DOCUMENTS

| CN | 2762381 Y | 3/2006 |
| CN | 102697445 A | 10/2012 |

(Continued)

OTHER PUBLICATIONS

Search Report for Application CN 2015800056419 in 2 pages.
(Continued)

*Primary Examiner* — Mathieu Vargot
(74) *Attorney, Agent, or Firm* — Knobbe, Martens, Olson & Bear, LLP

(57) ABSTRACT

The invention relates to a device for manufacturing an elongated hollow profile element that has at least one pulling wire (13), comprising:
two counter-bearings (11, 12), which are arranged on opposite sides of the device and which correspond to the elongated ends of the elongated hollow profile element, wherein one end of the at least one pulling wire (13) is anchored to the distal counter-bearing (11), and
a mold (2a, 2b), which forms a sealed elongated cavity (3) that can be filled with a hardening material, wherein the
(Continued)

cavity (3) extends between the two counter-bearings (11, 12) and the pulling wire (13) extends in the cavity (3) so as not to touch the cavity wall.

The invention further relates to a method for manufacturing an elongated hollow profile element that has at least one pulling wire (13), the elongated hollow profile element, and a bending section for an endoscope.

4 Claims, 4 Drawing Sheets

(51) Int. Cl.
| | | |
|---|---|---|
| A61B 1/00 | (2006.01) | |
| B60T 11/04 | (2006.01) | |
| F16C 1/26 | (2006.01) | |
| F16C 1/10 | (2006.01) | |
| F16D 125/60 | (2012.01) | |
| B29K 21/00 | (2006.01) | |
| B29L 31/00 | (2006.01) | |
| B62M 25/02 | (2006.01) | |

(52) U.S. Cl.
CPC .... *A61B 1/00071* (2013.01); *B29C 45/14754* (2013.01); *B60T 11/046* (2013.01); *F16C 1/10* (2013.01); *F16C 1/26* (2013.01); *B29K 2021/00* (2013.01); *B29L 2031/7542* (2013.01); *B62M 25/02* (2013.01); *F16C 2316/10* (2013.01); *F16C 2326/20* (2013.01); *F16C 2326/28* (2013.01); *F16D 2125/60* (2013.01)

(56) References Cited

U.S. PATENT DOCUMENTS

| | | |
|---|---|---|
| 4,241,729 A | 12/1980 | Aoshiro |
| 4,404,963 A | 9/1983 | Kohri |
| 4,415,767 A | 11/1983 | Gill et al. |
| 5,245,133 A | 9/1993 | DeCarlo et al. |
| 5,569,157 A | 10/1996 | Nakazawa et al. |
| 5,588,950 A | 12/1996 | Sano |
| 5,630,419 A | 5/1997 | Ranalletta |
| 6,383,132 B1 | 5/2002 | Wimmer |
| 6,547,722 B1 | 4/2003 | Higuma et al. |
| 6,582,361 B2 | 6/2003 | Hirano |
| 6,716,160 B2 | 4/2004 | Mitsumori |
| 7,179,223 B2 | 2/2007 | Motoki et al. |
| 7,198,599 B2 | 4/2007 | Goto et al. |
| 7,841,880 B2 | 11/2010 | Ikeda |
| 2001/0025135 A1 | 9/2001 | Naito et al. |
| 2002/0040180 A1 | 4/2002 | Hirano |
| 2002/0115907 A1 | 8/2002 | Mitsumori |
| 2003/0092965 A1 | 5/2003 | Konomura |
| 2004/0015050 A1 | 1/2004 | Goto et al. |
| 2006/0116550 A1 | 6/2006 | Noguchi |
| 2006/0135851 A1 | 6/2006 | Yamazaki |
| 2006/0199999 A1 | 9/2006 | Ikeda |
| 2006/0252993 A1 | 11/2006 | Freed |
| 2007/0156018 A1 | 7/2007 | Krauter et al. |
| 2007/0221701 A1 | 9/2007 | Ortiz |
| 2007/0282371 A1 | 12/2007 | Lee |
| 2009/0209820 A1 | 8/2009 | Tanaka |
| 2009/0286412 A1 | 11/2009 | Ikeda |
| 2010/0168560 A1 | 7/2010 | Hauck et al. |
| 2011/0288372 A1 | 11/2011 | Petersen |
| 2011/0313252 A1 | 12/2011 | Lin |
| 2012/0170767 A1 | 7/2012 | Astrom et al. |
| 2012/0209068 A1 | 8/2012 | Hosaka |
| 2014/0148646 A1 | 5/2014 | Inada |
| 2015/0057537 A1 | 2/2015 | Dillon et al. |
| 2015/0173711 A1 | 6/2015 | Hiraoka |

FOREIGN PATENT DOCUMENTS

| | | |
|---|---|---|
| CN | 202748535 U | 2/2013 |
| CN | 103153152 A | 6/2013 |
| CN | 103211566 a | 6/2013 |
| DE | 34 46 698 A1 | 7/1985 |
| DE | 196 27 016 C1 | 2/1998 |
| DE | 697 25 670 T2 | 7/2004 |
| DE | 101 48 099 B4 | 6/2006 |
| DE | 10 2009 060 500 | 7/2011 |
| DE | 102010034623 A1 | 2/2012 |
| DE | 10 2012 009332 | 11/2013 |
| EP | 0 028 396 B1 | 4/1981 |
| EP | 0055394 | 7/1982 |
| EP | 1475031 A1 | 11/2004 |
| EP | 1 759 626 A2 | 3/2007 |
| ES | 2356497 | 4/2011 |
| JP | S 61 118713 | 6/1986 |
| JP | S 62 227312 | 10/1987 |
| JP | H06254049 A | 9/1994 |
| JP | 10-225439 | 8/1998 |
| JP | H 11244225 | 9/1999 |
| JP | A-2001-061772 | 3/2001 |
| JP | 2001510696 | 8/2001 |
| JP | 2002 291699 | 10/2002 |
| JP | 2003 190085 | 7/2003 |
| JP | 2005 304 586 A | 11/2005 |
| JP | 2007 111541 | 5/2007 |
| JP | 2007 252921 | 10/2007 |
| JP | 2007313047 | 12/2007 |
| JP | 2009 505688 | 2/2009 |
| JP | 2009 101134 | 5/2009 |
| JP | 2009 530051 | 8/2009 |
| JP | 2009 201762 | 9/2009 |
| JP | 2012 245058 | 12/2012 |
| WO | WO 00/13569 A1 | 3/2000 |
| WO | WO 00/33727 | 6/2000 |
| WO | WO 2005/094665 | 10/2005 |
| WO | WO2008056642 A1 | 5/2008 |
| WO | WO 2009/008596 | 1/2009 |
| WO | WO 2011/108157 | 9/2011 |
| WO | WO 2011/114772 A1 | 9/2011 |
| WO | WO 2013/129204 | 9/2013 |

OTHER PUBLICATIONS

Search Report for Application CN 2014800410593 in 2 pages.
Office Action dated Sep. 4, 2017 in 7 pages for Chinese Application No. 201580005641.9.
Oct. 8, 2014 Int'l Search Report from related PCT App. No. PCT/EP2014/065587 (4 pgs).
Jan. 13, 2015 Int'l Search Report from related PCT App. No. PCT/EP2014/073064 (4 pgs).
Jan. 19, 2015 Int'l Search Report from related PCT App. No. PCT/EP2014/073065 (6 pgs).
Mar. 2, 2015 Int'l Search Report from related PCT App. No. PCT/EP2014/077938 (3 pgs).
Mar. 24, 2015 Int'l Search Report from related PCT App. No. PCT/EP2014/075902 (4 pgs).
Mar. 24, 2015 Int'l Search Report from related PCT App. No. PCT/EP2015/051252 (4 pgs).
Apr. 30, 2015 Int'l Search Report from related PCT App. No. PCT/EP2015/051245 (6 pgs).
Jan. 13, 2015 Int'l Search Report from related PCT App. No. PCT/EP2014/073066 (4 pgs).
Anonymous: "Products I BMP-TAPPI", Jun. 30, 2013 (Jun. 30, 2013), XP055394249, Gefunden im Internet: URL:https://web.archive.org/web/20130630082009/http :// www.bmp-tappi.com:80/products [gefunden am Jul. 27, 2017].
Anonymous: "10. Tappo per innesti rapidi femmina", Jun. 22, 2013 (Jun. 22, 2013), XP055394266, Gefunden im Internet: U RL :https ://web.arch ive.o rglwebl 201 306221 61 7 34lhTtpl www. bmp-tappi. it:80/po rtfol io_item/tappo-per-i n nesti- rapidifemmina [gefunden am Jul. 27, 2017].
International Search Report from PCT/EP2014/077938 in 3 pages.

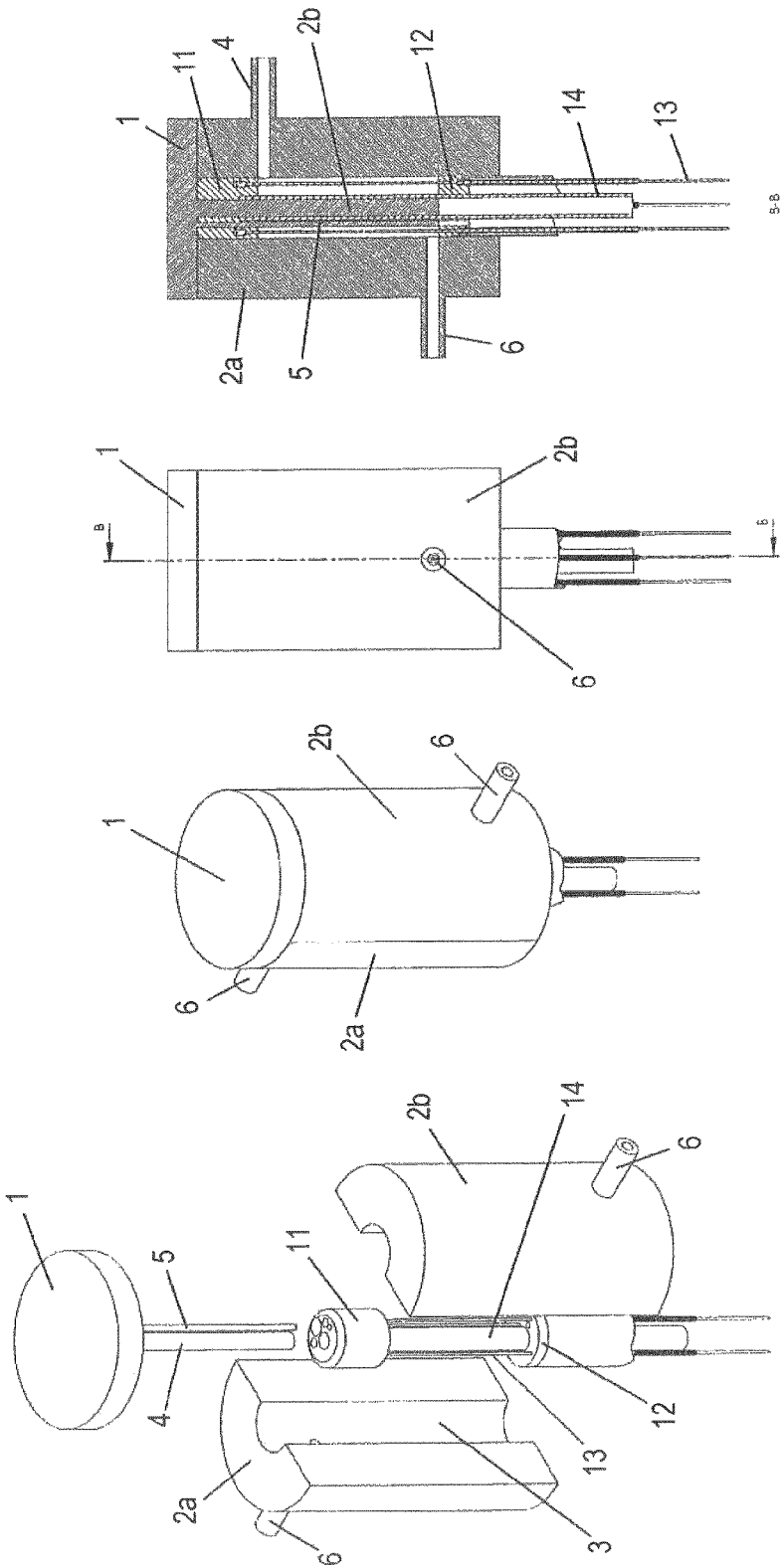

DEVICE AND A METHOD FOR MANUFACTURING AN ELONGATED HOLLOW PROFILE ELEMENT, AN ELONGATED HOLLOW PROFILE ELEMENT, AND A BENDING SECTION FOR AN ENDOSCOPE

BACKGROUND OF THE INVENTION

Field of the Invention

The present invention relates to a device and a method for manufacturing an elongated hollow profile element, an elongated hollow profile element and a bending section for an endoscope. In particular, the present invention relates to such an elongated hollow profile element that is bendable and surrounds an inner element extending therethrough.

Such an elongated hollow profile element is e.g. used as wire guide for a bicycle brake or bicycle gearshift. Moreover, such elongated hollow profile elements are used in a bending section for an endoscope.

Namely, in an endoscope, a bendable end of a catheter, i.e. a so-called deflecting portion as bending section, is moved by pivoting a control element, which e.g. operates pulling cable elements, which are connected to the head of the deflecting portion. Hence, the movement of the deflecting portion is to precisely follow the movement of the control element. In this deflecting portion, an elongated hollow profile element surrounds the inner elements of the deflecting portion, such as the pulling cable elements, a working channel, etc.

Description of the Related Art

In the case of medical examinations by means of an endoscope, the transfer of a pivoting movement of a control element to a bending movement of the deflecting portion should be as precise as possible. On the other hand, it should be easy and clear to the user to transfer a pivoting movement of a control element to a bending movement of the deflecting portion.

SUMMARY OF THE INVENTION

It is an object of the present invention to provide an improved device and an improved method for manufacturing an elongated hollow profile element. Moreover, an elongated hollow profile element and a bending section for an endoscope shall be provided.

According to the invention a device is provided comprising at least one axial opening in which a pulling wire is arranged axially relative to the hollow profile element in a pullable manner, comprising: two counter-bearings which are arranged on opposite sides of the device and which correspond to the elongated end of the elongated hollow profile element, wherein one end of the at least one pulling wire is anchored to the distal counter-bearing, and a mold which forms a sealed elongated cavity that can be filled with a hardening material forming the hollow profile element, wherein the cavity extends between the two counter-bearings and the pulling wire extends in the cavity so as not to touch the cavity wall, wherein, at the end of the manufacture, the at least one pulling wire remains arranged in a pullable manner in the hardened material axially relative to the hollow profile element.

According to the invention a method is provided for manufacturing an elongated hollow profile element comprising at least one axial opening in which a pulling wire is arranged axially relative to the hollow profile element in a pullable manner, the pulling wire being used for transmitting a pivoting movement of a control element to a bending section, comprising the steps of: providing a mold which forms a sealed elongated cavity that can be filled with a hardening material, wherein the cavity extends between two counter-bearings that seal the cavity; inserting at least one pulling wire into the mold such that one end of the at least one pulling wire is anchored to the distal counter-bearing, wherein the pulling wire extends in the cavity so as not to touch the cavity wall; filling the cavity with a hardening material for forming the hollow profile manufacturing process, the at least one pulling wire remains arranged in a pullable manner in the hardened material relative to the hollow profile element.

The invention also provides an elongated hollow profile element manufactured by the aforesaid method.

The invention further provides a bending section for an endoscope comprising a sheath formed such an elongated hollow profile element.

Advantageous further developments are described herein.

Thus, the invention relates to a device for manufacturing an elongated hollow profile element which comprises at least one pulling wire, including: two counter-bearings which are arranged on opposite sides of the device and which correspond to the elongated ends of the elongated hollow profile element, wherein one end of the at least one pulling wire is anchored to the distal counter-bearing, and a mold which forms a sealed elongated cavity that can be filled with a hardening material, wherein the cavity extends between the two counter-bearings and the pulling wire runs in the cavity so as not to touch the cavity wall.

In the device, the counter-bearings can be spaced apart such that the pulling wire is tensioned. Due to this, the pulling wire or the pulling wires can extend, in a predefined manner, in a straight direction between the counter-bearings. Thus, after the material to be filled in has hardened, there are pulling wire channels that are straight. The pulling wires are already arranged in the pulling wire channels.

Besides, in the device, not only the at least one pulling wire can be arranged in the cavity, but also at least one tube element for forming a working channel such that the ends of the at least one tube element are anchored in the counter-bearings, respectively.

Alternatively, in the device, not only the at least one pulling wire can be arranged in the cavity, but also at least one removable mandrel for forming a working channel such that the ends of the at least one mandrel are anchored in the counter-bearings, respectively.

In the device, the mandrel can have an off-center end portion at its distal end. That is, the mandrel can be formed such that it has a proximal end portion which is positioned in the middle with respect to the mold and the cavity, i.e. on the longitudinal axis/central axis of the mold and the cavity, which can be coaxial to each other, and a distal end portion, which is off-center with respect to the mold and the cavity, i.e. it does not end on the longitudinal axis/central axis of the mold and the cavity. Hence, the mandrel can be bent between the proximal end portion and the distal end portion, the point of bending being situated on the central axis of the mold and the cavity. The mandrel may also have a bend between the proximal end portion and the distal end portion. The mandrel can also be multiply angled and/or bent between the proximal end portion and the distal end portion.

Furthermore, in the device, at least one cable element for transmitting signals can be arranged in the cavity such that the ends of the at least one cable element are anchored in the counter-bearings, respectively.

In the device, all pulling wires, tube elements or mandrels and cable elements can extend in parallel to the longitudinal extension of the cavity.

In the device, all pulling wires can extend in parallel to the longitudinal extension of the cavity, and the tube elements and cable elements are arranged in the cavity in a spiral-like manner.

In the device, the at least one pulling wire can have a coating which repels the hardening material to be filled into the cavity.

In the device, the mold can consist of several mold pieces each forming a circular segment in cross-section; said mold pieces can be pushed towards each other, and, in their pushed-together state, the entire inner space of the mold pieces forms the cavity.

In the device, the mold can consist of several shell-like mold pieces of a circular segment type, at least one of which comprises at least one access channel for the hardening material to be filled in.

In the device, the mold can consist of one single elongated hollow profile whose inner space forms the cavity.

At least one of the counter-bearings can be a retaining cap in which the at least one pulling wire is removably fittable, and the respective retaining cap can be supported on a die.

In the device, the cavity can be cylindrical or polygonal in cross-section.

In the inventive method for manufacturing an elongated hollow profile element comprising at least one pulling wire, the following steps are taken: providing a mold which forms a sealed elongated cavity that can be filled with a hardening material, wherein the cavity extends between two counter-bearings that seal the cavity; inserting at least one pulling wire into the mold such that one end of the at least one pulling wire is anchored to the distal counter-bearing, wherein the pulling wire runs in the cavity so as not to touch the cavity wall; filling the cavity with a hardening material; curing the hardening material; and opening the mold.

In the method, after opening the mold, the at least one pulling wire can be pulled such that the pulling wire gets disengaged from the hardened material surrounding it and a movement channel for the pulling wire is formed.

The hardening material can be an elastomer.

The elastomer can be silicone, a natural rubber or a silicone rubber.

The elongated hollow profile element can be a bending section for an endoscope.

The elongated hollow profile element can be a wire guide for a Bowden cable of a bicycle brake or a bicycle gearshift.

The features of the invention can be suitably combined.

Below, the invention is described in detail by means of examples by reference to the drawings, which illustrate some embodiments of the invention.

BRIEF DESCRIPTION OF THE DRAWINGS

FIG. 4 shows a device for manufacturing the elongated hollow profile element according to the invention, FIG. 4A showing a perspective exploded view, FIG. 4B a perspective view, FIG. 4C a lateral view, and FIG. 4D a sectional view.

DETAILED DESCRIPTION OF THE INVENTION

Some embodiments of the present invention are described below.

First Embodiment

First of all, a first embodiment is described with reference to the drawings.

Figure 1A:
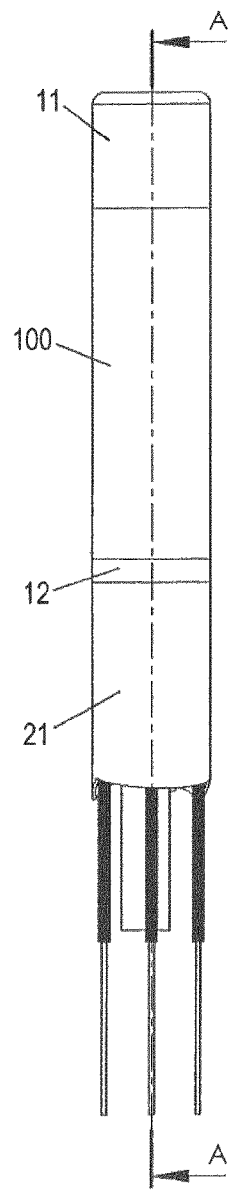
FIG. 1 shows an application example of an elongated hollow profile element according to the invention, FIG. 1A showing a lateral view, FIG. 1B a sectional view, and FIG. 1C a perspective view.
Figure 1B:
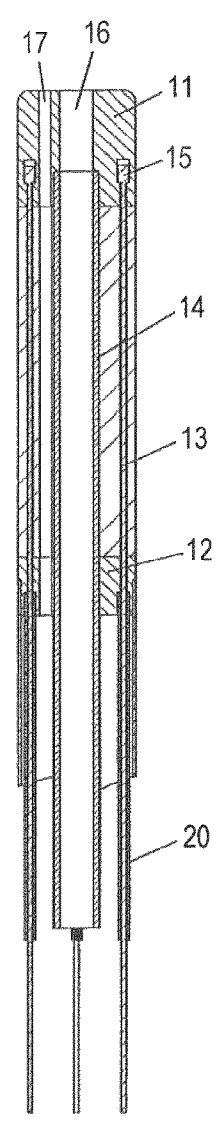
Figure 1C:
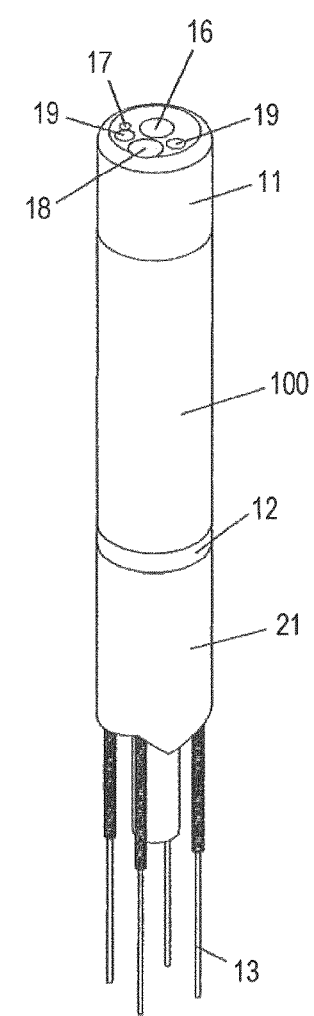

FIG. 1 shows an application example of an elongated hollow profile element according to the invention, FIG. 1A showing a lateral view, FIG. 1B a sectional view along A-A in FIG. 1A, and FIG. 1C a perspective view.

In the first embodiment, the present invention is used for a sheath element of a bending section (also named deflecting portion) for an endoscope. The sheath element is an elongated hollow profile element within the terms of the invention.

Below, such a bending section is explained in greater detail by means of FIGS. 1 and 2.

At its distal end, the bending section has an endoscope head 11 in which e.g. a non-depicted camera and non-depicted LEDs are arranged. In the proximal direction of the bending section, an elongated hollow profile element 100 is arranged at the proximal side of the endoscope head 11 and, inside, has several pulling cables 13 running in the longitudinal direction of the elongated hollow profile element 100. In the present example, four pulling cables 13 are provided in the elongated hollow profile element 100. Alternatively, three, five or more pulling cables 13 can be provided.

An intermediate piece 12 is arranged on the proximal side of the elongated hollow profile element 100 and is used for anchoring spiral sleeves 20 for pulling cables, in which spiral sleeves 20 the pulling cables 13 run proximally from the intermediate piece 12. The intermediate piece 12 is constructed as an annular element.

At the proximal side of the intermediate piece 12, a catheter tube 21 is arranged, leading to an endoscope operating part. The catheter tube 21 surrounds the pulling cable spiral sleeves 20, in which the pulling cables 13 slidably run.

Thus, the bending section extends from the annular element 12 on the proximal side of the bending section to the endoscope head 11 at the distal side of the bending section.

Below, the elements of the bending section are described in more detail.

The endoscope head 11 can be a plastic carrier made of an organic polymeric material, which can e.g. be produced by injection molding. The endoscope head 11 e.g. consists of a thermoplastic or a duroplastic. In particular, the endoscope head 11 can be produced from polypropylene (PP), acrylonitrile butadiene styrene (ABS), polycarbonate (PC), polyethylene terephthalate (PET), polybutylene terephthalate (PBT), polyamide (PA), polyphenylene sulfide (PPS), polysulfone (PSU), polyethersulfone (PES), polyetherimide (PEI), etc. These specifications are merely examples and other materials can be used for the endoscope head 11.

The endoscope head 11 has distal openings 19-19 on its distal front face. In particular, these openings can be a distal opening of a working channel 16, a distal opening of a flushing channel 17, a camera window 18 and one or more LED windows 19. The camera window 18 is used for a signal input for a non-depicted camera, and the LED window 19 is used for a signal output for a non-depicted LED chip.

Thus, the endoscope head 11 comprises a working channel 16 and at least one flushing channel 17. In the present example, the endoscope head 11 comprises one flushing channel 17. The endoscope head 11 may, however, have plural flushing channels. More precisely, the working channel 16 and the flushing channel 17 are provided in the endoscope head 11 in the axial direction in parallel to the central axis of the endoscope head 11. As is shown in FIG. 1B and FIG. 1C, the flushing channel 17 is arranged radially outside of the working channel 16, but the invention is not restricted thereto.

At a distance to its proximal end surface, the endoscope head 11 has, on its outer circumferential surface, respective cavities for pulling cable anchoring bodies 15. Such a pulling cable anchoring body 15 may have different shapes, it may be a barrel nipple, a pear nipple, a ball nipple, etc. In the present example, the pulling cable anchoring body 15 is a barrel nipple. Each of the cavities is dimensioned such that there is enough space for a pulling cable anchoring body 15 and has, on its proximal side, a supporting surface area on which the pulling cable anchoring body 15 can be supported in the proximal direction. Thus, the supporting surface area extends horizontally, i.e. in parallel to the proximal end surface of the endoscope head 11. The cavities are adapted to the shape of the pulling cable anchoring body 15 and, in the present example, are designed in the form of a cylinder. Thus, in the present example, the endoscope head 11 has four such supporting surface areas. Each supporting surface area is centrically provided with a channel-type groove extending toward the proximal end surface of the endoscope head 11; when the pulling cable anchoring body 15 is inserted at the supporting surface area, said groove receives the pulling cable 13 connected to the pulling cable anchoring body 15. The diameter of the supporting surface area is, in any case, larger than the diameter of the pulling cable 13. Should e.g. a quadrangular pulling cable anchoring body be used, so that the cavity has a quadrangular shape, a square supporting surface area is obtained.

A pulling cable anchoring body 15 is inserted into each lateral cavity on the endoscope head 11 such that its proximal side abuts on the supporting surface area, so that a pulling force acting in the proximal direction is transferred from the pulling cable anchoring body 15 to the supporting surface area and, thus, to the endoscope head 11. Every pulling cable anchoring body 15 is firmly arranged on the distal end of a pulling cable 13 in the known manner.

In the endoscope head 11, the working channel 16 extends along its longitudinal axis from the proximal to the distal direction. On the proximal side of the endoscope head 11, the endoscope head 11 has a diametrically widened portion at the entry for the working channel 16. A tube element 14 is inserted into said diametrically widened portion. At its inner circumferential surface, the tube element 14 forms a section of the working channel 16, as is shown in FIG. 1B. The tube element 14 can be glued or fitted into the endoscope head 11, or can be fastened otherwise.

The elongated hollow profile element 100 according to the invention is a tubular construction radially surrounding the working channel 16. In the present example, the elongated hollow profile element 100 surrounds the working channel 16 such that the tube element 14 is arranged between the working channel 16 and the elongated hollow profile element 100. In an alternative, the tube element 14 can also be omitted. Then, the elongated hollow profile element 100 forms the working channel 16 directly on the inner circumferential side. The elongated hollow profile element 100 consists of an elastomer. In particular, silicone, a natural rubber or a silicone rubber, etc. can be used for the elongated hollow profile element 100.

At its distal side, the elongated hollow profile element 100 tightly abuts on the endoscope head 11. At its proximal side, the elongated hollow profile element 100 tightly abuts on the intermediate piece 12. The pulling cables 13 are arranged along its longitudinal extension inside the elongated hollow profile element 100 in parallel to the longitudinal axis of the elongated hollow profile element 100. Therefore, in the elongated hollow profile element 100, axial continuous openings, in which the pulling cables 13 run, have been created according to the invention between the inner circumference and the outer circumference. The axial continuous openings for the pulling cables 13 are arranged in the elongated hollow profile element 100—viewed perpendicularly to the axis of the elongated hollow profile element 100—on an imaginary circle spaced apart less from the outer circumference than from the inner circumference of the elongated hollow profile element 100. Thus, the pulling cables 13 are protected and guided in the elongated hollow profile element 100 between the intermediate piece 12 and the endoscope head 11. In the present example, four axial continuous openings are provided for four pulling cables 13 in the elongated hollow profile element 100. In the respective axial continuous opening for the pulling cables 13, the respective pulling cable 13 can be axially pulled relative to the axial continuous opening by which it is surrounded.

In the present example, the elongated hollow profile element 100 has, as flushing channel 17, a continuous channel which axially extends in parallel to the working channel 16 and the four axial continuous openings for the pulling cables 13. The flushing channel in the elongated hollow profile element 100 is provided in the elongated hollow profile element 100 between the working channel 16 and the imaginary circle on which the axial continuous openings for the pulling cables 13 are arranged.

At its proximal side, the intermediate piece 12 has blind holes for anchoring the pulling cable spiral sleeves 20. In the intermediate piece 12, the pulling cable spiral sleeves 20 are inserted from the proximal side of the intermediate piece 12. Preferably, the pulling cable spiral sleeves 20 are firmly connected to the intermediate piece 12. They can be glued in, for example. The diameter of the blind holes in the intermediate piece 12 may also be selected such that the pulling cable spiral sleeves 20 are press-fitted into the same.

The intermediate piece 12 has an axial centric inner opening through which the working channel runs. Therefore, in the present example, the pressure-resistant tube element 14 for the working channel is arranged in the inner opening of the intermediate piece 12.

The centric inner opening for the tube element 14 and a lateral through-hole for the flushing channel 17 are provided in the intermediate piece 12 in the axial direction in parallel to the central axis of the intermediate piece 12. As is shown in FIG. 1B, the lateral through-hole for the flushing channel 17 is arranged radially outside the centric inner opening. The arrangement of the lateral through-hole for the flushing channel 17 and the centric inner opening for the tube element 14 of the working channel 16 correspond to the arrangement of the flushing channel 17 and the working channel 16 in the endoscope head 11.

Figure 2:
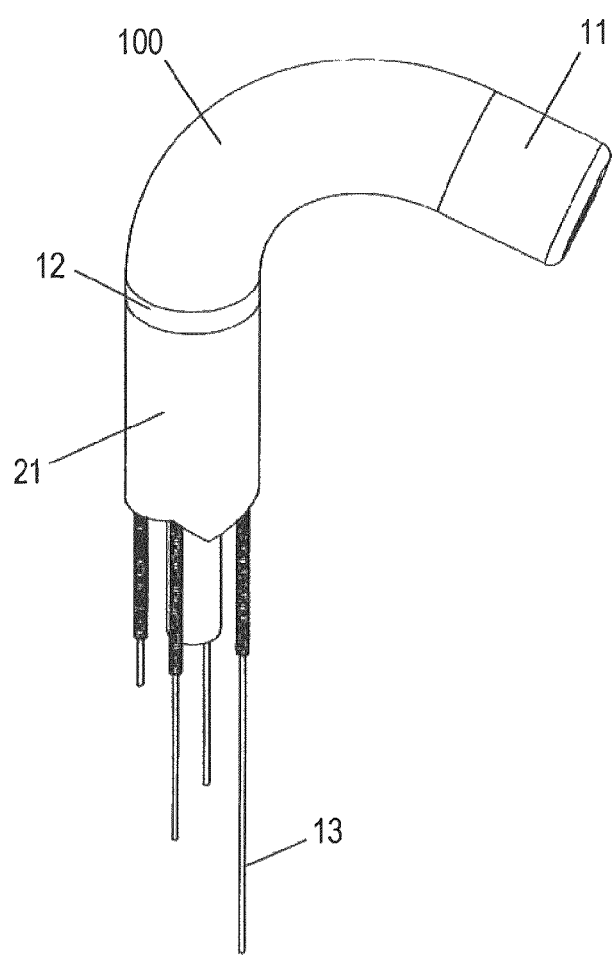
FIG. 2 shows a perspective view of the application example of FIG. 1 in a bent state.

FIG. 2 shows a perspective view of the application example of FIG. 1 in a bent state.

The endoscope head 11 can be pivoted in any direction in a known manner by means of a pulling movement on the pulling cables 13 by a non-depicted control element. As it is shown in the drawing, the right pulling cable 13 is pulled more in the proximal direction than the front pulling cable and the rear pulling cable so that the endoscope head 11 tilts to the right and pulls the left pulling cable 13 anchored thereto in the distal direction.

Figure 3:
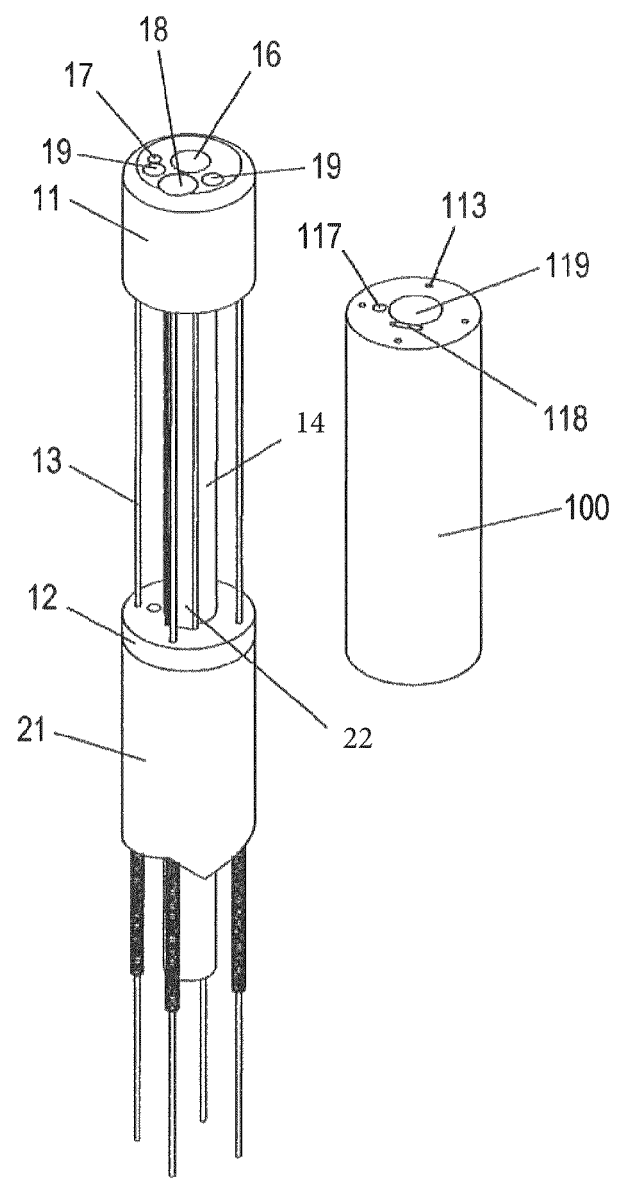
FIG. 3 shows a perspective view of the application example of FIG. 1, the elongated hollow profile element according to the invention being shown separately.

FIG. 3 shows a perspective view of the application example of FIG. 1, the elongated hollow profile element according to the invention being shown separately.

In particular, FIG. 3 shows the first embodiment in which the bending section without the elongated hollow profile element and the elongated hollow profile element 100 are shown separately. In other words, the elongated hollow profile element 100 is not shown in its post-assembly position for reasons of better clarity.

The representation of the bending section corresponds to the representation of FIG. 1C, wherein the inside in the area of the elongated hollow profile element 100 is shown. In particular, a cable 22 for the camera is shown as well. The cable 22 extends, similarly to the flushing channel 17, axially in the elongated hollow profile element 100 in parallel to the working channel 16 and the four axial continuous openings for the pulling cables 13. In the present example, the cable 22 has a flat shape with a rectangular cross-section, to which the channel 118 in the elongated hollow profile element 100 is adapted. The channel 118 in the elongated hollow profile element 100 is provided between the working channel 16 and the imaginary circle, on which the axial continuous openings for the pulling cables 13 are arranged, in the elongated hollow profile element 100.

On its proximal side and its distal side (only the distal side can be recognized in FIG. 3), the elongated hollow profile element 100 comprises four openings 113 for the pulling cables 13, an opening 117 for the flushing channel 17, an opening 118 for the cable 22 of the camera and an opening 119 for the working channel 18.

Manufacture of the Elongated Hollow Profile Element

In the following, the manufacture of the elongated hollow profile element 100 is described.

FIG. 4 shows a device for manufacturing the elongated hollow profile element according to the invention, FIG. 4A showing a perspective exploded view, FIG. 4B a perspective view, FIG. 4C a lateral view and FIG. 4D a sectional view.

The bending section is kept available in a state in which it has been fully assembled except for the elongated hollow profile element 100. The bending section in said state is subsequently designated as raw bending section.

A mold which, in the present example, consists of two half molds 2a and 2b, has on its inside a cylindrical extension as the counter-mold for the outer circumference of the elongated hollow profile element 100. The outer diameters of the endoscope head 11, the elongated hollow profile element 100 and the intermediate piece 12 are identical, and the inner diameter of the cylindrical extension is adapted to this outer diameter of the endoscope head 11, the elongated hollow profile element 100 and the intermediate piece 12.

The half molds 2a and 2b each have a semi-circular cross-section and, together, form a hollow cylinder whose inner space forms a cavity 3 for the manufacture of the elongated hollow profile element 100. The cavity 3 is cylindrical. Its inner shape is adapted to the outer shape of the elongated hollow profile element 100.

The half molds 2a and 2b can be pushed towards and away from each other. When being pushed together, the cavity 3 is closed at its circumference.

In other words, the mold consists of several mold pieces 2a and 2b, each forming a semi-circle in cross-section, and being movable towards each other, wherein, when being pushed together, the entire inner space of the mold pieces forms the cavity 3.

The bending section in the state in which it is fully assembled except for the elongated hollow profile element 100, i.e. the raw bending section, is inserted into the cavity 3 in such a way that the distal front face of the endoscope head 11 is aligned with the distal front face of the mold pieces 2a and 2b, as can be seen in FIG. 4D. When inserted in the cavity 3, the endoscope head 11 and the intermediate piece 12 of the bending section form counter-bearings, respectively, which tension the pulling cables 13 running therein and between which the elongated hollow profile element 100 is to be created. The endoscope head 11 forms a first counter-bearing and the intermediate piece 12 forms a second counter-bearing. Each counter-bearing represents a retaining cap which makes sure that the pulling cables 13 can be kept tensioned.

In the area of the cavity 3 of the mold pieces 2a and 2b, when the endoscope head 11 and the intermediate piece 12 are inserted, a radial opening is provided in each mold piece 2a and 2b between the endoscope head 11 and the intermediate piece 12, such that it radially penetrates the wall of the mold pieces 2a and 2b. On the outer side of the mold pieces 2a and 2b the opening continues into an access pipe. The opening and the access pipe each form an access channel element 6 for filling the cavity 3 with the hardening material to be filled in for the elongated hollow profile element 100. In the present example, the access channel element 6 of the mold piece 2a is located further on the distal side and the access channel element 6 of the mold piece 2b is located further on the proximal side.

A disk-type die 1 is placed on the distal front face of the endoscope head 11 and on the distal front face of the mold pieces 2a and 2b. On its proximal side the disk-type die 1 has a stabilization body 4 for the tube element 14 for the working channel and a mold element 5 for the flushing channel. The one stabilization body 4 and the mold element 5 extend perpendicularly to the disk-type die 1. More explicitly, the stabilization body 4 is arranged on the central axis of the disk-type die 1 and the mold element 5 is arranged adjacent and in parallel to the stabilization body 4. The position of the stabilization body 4 and the mold element 5 is chosen in such a manner that the mold element 5 forms the flushing channel while the stabilization body 4 forms the working channel or supports the tube element 14 from the inside for forming the working channel.

When the mold halves 2a and 2b are closed with the raw bending section being inserted, the disk-type die 1 is pushed from the distal side onto the distal front faces of the mold halves 2a and 2b such that the stabilization body 4 enters into the tube element 14, as can be gathered from FIGS. 4A to 4D. Thus, the form is closed. In this state, the pulling wire 13 runs in the cavity 3 so as not to touch the cavity wall.

Now, the elastomer material forming the elongated hollow profile element 100 is poured into the mold. Particularly, the elastomer material is poured through one of the two access channel elements 6, while the access channel element 6 serves as air discharge opening through which the air in the cavity 3, which is displaced by the poured in elastomer material, can escape. When the inner space of the mold is filled with elastomer material, e.g. when the elastomer material emerges through the access channel element 6 used as air discharge opening, or when a sensor at the inside inlet of the access channel element 6 used as air discharge opening indicates a presence of elastomer material, the access channel elements 6 are closed.

The elastomer material hardens. Thereupon, the mold is opened and the bending section is removed. Elastomer material, which is still present at the outer circumference of the elongated hollow profile element 100 and which corresponds to the inner space of the access channel elements 6, is cut off. Alternatively, a slide blocking the respective access channel element 6 after filling in the elastomer material can be arranged on each mold 2a, 2b on the inner circumference of the cavity 3 in the area where the access channel elements 6 merge into the cavity 3.

After opening the mold 2a, 2b, the pulling cables 13 are pulled in such a manner that the pulling cables 13 get disengaged from the elastomer material surrounding them. Thus, a movement channel for the pulling cables 13 is formed. Preferably, the pulling cables 13 are provided with a coating repelling the elastomer material.

Thus, a bending section which has an elongated hollow profile element 100 in which pulling cables 13 are guided and a working channel extends is created. The elongated hollow profile element 100 is a sheath element of the bending section.

Second Embodiment

In the first embodiment, the present invention is used for a sheath element of a bending section for an endoscope.

In the second embodiment not depicted in the drawings, the present invention is used for a wire guide for a Bowden cable of a bicycle brake or a bicycle gearshift.

In this connection, the wire guide is the elongated hollow profile element within the meaning of the invention. The wire guide for the bicycle brake or the bicycle gearshift is constructed in a similar manner as the elongated hollow profile element 100 of the first embodiment, but does not comprise a working channel on its central axis, but has the guided wire for the bicycle brake or the bicycle gearshift on its central axis.

Other counter-bearings instead of the endoscope head 11 and the intermediate piece 12, can be used wherein the wire guide comprises counter-bearings to which the wire cable element is centrically fitted. The length of the elongated hollow profile element is adapted as needed and the length of the mold is chosen accordingly.

The manufacturing method is similar as in FIGS. 4A to 4D, however, the stabilization body 4 and the mold element 5 are not provided.

After opening the mold 2a, 2b, the one pulling cable is pulled such that the pulling cable gets disengaged from the elastomer material surrounding the same. In this way, a movement channel for the pulling cable is formed.

Thus, a wire guide for a bicycle brake or a bicycle gearshift is created.

Alternatives

In the first example, a camera and LED elements are arranged in the endoscope head 11. Alternatively, an ultrasonic emitting means can be arranged instead of the LED elements, and an acoustic sensor instead of the camera.

In the first example, the tube element 14 forms a section of the working channel 16 at its inner circumferential surface. The distal end portion of the working channel 16 is formed in the endoscope head 11 without the tube element 14 as a hole in the endoscope head 11. Alternatively, the tube element 14 can extend up to the distal end side of the endoscope head 11.

In another alternative, the tube element 14 in the area between the endoscope head 11 and the intermediate piece 12 need not be provided. In this case, the tube element 14 can end in the intermediate piece 12.

In this case, the construction can be chosen such that the working channel 16 is only formed by a mandrel 4. The mandrel 4 corresponds to the stabilization body 4 of FIG. 4A. The diameter of the mandrel 4 is adapted to the end diameter to be formed of the working channel.

The arrangement of the channels in the endoscope head 11 is not restrictive and can be modified as needed.

In the example of FIG. 4, the mold consists of several mold pieces 2a and 2b, each forming a semi-circle in cross section, and being adapted to be pushed towards each other, wherein, when being pushed together, the entire inner space of the mold pieces forms the cavity 3. The mold can also consist of three or more mold pieces, each forming a circular segment in cross-section and adapted to be pushed towards each other, wherein, when being pushed together, the entire inner space of the mold pieces forms the cavity 3. In another alternative, the mold consists of one single elongated hollow profile whose inner space forms the cavity 3.

Not every mold piece has to have an access channel. It is sufficient that the mold, when consisting of several shell-like mold pieces of a circular-segment-type, comprises at least one mold piece having an access channel for the hardening material to be filled in.

In the first example, the mandrel 4 extends perpendicularly from the die 1 which basically forms a lid of the mold 2a, 2b. Thus, in the first example, the mandrel 4 is located on the central axis of the mold 2a, 2b. In this way, a straight working channel 16 is formed, which extends centrically in the bending section. Alternatively, the mandrel 4 can have a proximal end portion extending on the central axis of the mold 2a, 2b, and a distal end portion extending at an angle to the central axis of the mold 2a, 2b and being attached to the die 1 off-centered to the central axis of the mold 2a, 2b.

That is, the mandrel 4 can be bent between the proximal end portion and the distal end portion, the point of bending being situated on the central axis of the mold 2a, 2b and the cavity 3. The mandrel 4 may also have a bend with a radius between the proximal end portion and the distal end portion. The mandrel 4 may even be multiply angled and/or bent or meander between the proximal end portion and the distal end portion. Since the elastomer material is elastic also after hardening, the mandrel 4 can be extracted from the formed and hardened elongated hollow profile element 100 without any problems, even if the mandrel 4 is angled, bent or meandering. Thereby, a working channel 16 can be created which, at its distal end, does not end centrically, but off-centered on the distal surface of the endoscope head 11. Thus, more room is available for a camera and a camera window 18, which can be arranged closer to the center than in the first example.

If needed, the mold element 5 for the flushing channel 17 can be angled, bent or meandering in a similar manner.

LIST OF REFERENCE SIGNS 1 die
2a, 2b mold
3 cavity
4 stabilization body; mandrel
5 mold element for flushing channel
6 access channel element
11 endoscope head; first counter-bearing
12 intermediate piece; second counter-bearing 13 pulling cable
14 tube element for working channel
15 pulling wire anchoring body
16 working channel
17 flushing channel
18 camera window
19 LED window
20 spiral sleeve for pulling cable
21 catheter tube
22 cable for camera
100 elongated hollow profile element
113 openings for the pulling cables 13
117 opening for flushing channel 17
118 opening for cable 22
119 opening for working channel 16

What is claimed is:

1. A method for manufacturing an elongated hollow profile element comprising at least one axial opening in which a pulling wire is arranged axially relative to the hollow profile element in a pullable manner, the pulling wire being used for transmitting a pivoting movement of a control element to a bending section, comprising the steps of:
   providing a mold which forms a sealed elongated cavity that can be filled with a hardening material, wherein the cavity extends between two counter-bearings that seal the cavity;
   inserting at least one pulling wire into the mold such that one end of the at least one pulling wire is anchored to the distal counter-bearing, wherein the pulling wire extends in the cavity so as not to touch the cavity wall;
   filling the cavity with a hardening material for forming the hollow profile element;
   curing the hardening material; and
   opening the mold,
   wherein, at the end of the manufacturing process, the at least one pulling wire remains arranged in a pullable manner in the hardened material relative to the hollow profile element.

2. The method according to claim 1, comprising the step of:
   after opening the mold;
   pulling the at least one pulling wire such that the pulling wire gets disengaged from the hardened material surrounding it and a movement channel for the pulling wire is formed.

3. The method according to claim 1, wherein the hardening material is an elastomer.

4. The method according to claim 3, wherein the elastomer is silicone, a natural rubber or a silicone rubber.

* * * * *

UNITED STATES PATENT AND TRADEMARK OFFICE
CERTIFICATE OF CORRECTION

PATENT NO. : 9,955,856 B2  
APPLICATION NO. : 15/106268  
DATED : May 1, 2018  
INVENTOR(S) : Thomas Viebach Page 1 of 1

It is certified that error appears in the above-identified patent and that said Letters Patent is hereby corrected as shown below:

On the Title Page

In Column 1 (Notice) at Line 3, After "0 days." delete "days.".

In the Specification

In Column 1 at Line 55, Change "end" to --ends--.

In Column 2 at Line 13, After "profile" insert --element; curing the hardening material; and opening the mold, wherein, at the end of the--.

In the Claims

In Column 12 at Line 16 (approx.), In Claim 2, change "mold;" to --mold:--.

Signed and Sealed this  
Thirty-first Day of July, 2018

Andrei Iancu  
*Director of the United States Patent and Trademark Office*